(12) United States Patent
Ryan et al.

(10) Patent No.: US 7,634,936 B2
(45) Date of Patent: Dec. 22, 2009

(54) METHOD AND SYSTEM FOR SAMPLING DISSOLVED GAS

(75) Inventors: M. Cathryn Ryan, Calgary (CA); Kimberly L. McLeish, Cochrane (CA); Angus Chu, Calgary (CA)

(73) Assignee: UTI Limited Partnership, Calgary (CA)

( * ) Notice: Subject to any disclaimer, the term of this patent is extended or adjusted under 35 U.S.C. 154(b) by 226 days.

(21) Appl. No.: 11/674,716

(22) Filed: Feb. 14, 2007

(65) Prior Publication Data

US 2008/0216591 A1  Sep. 11, 2008

Related U.S. Application Data

(60) Provisional application No. 60/774,208, filed on Feb. 17, 2006.

(51) Int. Cl.
*G01N 1/22* (2006.01)
*G01N 1/28* (2006.01)

(52) U.S. Cl. .............. 73/23.41; 73/19.02; 73/19.1; 73/31.07; 73/863.23

(58) Field of Classification Search ............. 73/19.01, 73/19.02, 19.09, 19.1, 19.12, 31.07, 863.23, 73/23.41
See application file for complete search history.

(56) References Cited

U.S. PATENT DOCUMENTS

| | | | |
|---|---|---|---|
| 3,062,056 A | 11/1962 | Wicoff | |
| 5,010,776 A | 4/1991 | Lucero et al. | 73/863.23 |
| 5,046,568 A | 9/1991 | Cordry | |
| 5,487,431 A | 1/1996 | Webb | |
| 5,804,743 A | 9/1998 | Vroblesky et al. | 73/863.23 |
| 5,922,974 A | 7/1999 | Davison et al. | |
| 6,272,938 B1 | 8/2001 | Baghel et al. | |
| 2004/0129058 A1 | 7/2004 | Boyd et al. | |
| 2004/0177672 A1 | 9/2004 | Schmitt et al. | |

FOREIGN PATENT DOCUMENTS

CA  2 401 375  8/2001

OTHER PUBLICATIONS

PCT International Search Report and Written Opinion, issued in International Application No. PCT/IB2007/002640, dated Feb. 6, 2008.
Castro et al., "Noble gases as natural tracers of water circulation in the Paris Basin 2. Calibration of a groundwater flow model using noble gas isotope data," *Water Resources Research*, 34:2467-2484, 1998.
Dunkle et al., "Chlorofluorocarbons ($CCl_3F$ and $CCl_2F_2$) as dating tools and hydrologic tracers in shallow groundwater of the Delmarva Peninsula, Atlantic Coastal Plain, United States," *Water Resources Research*, 29:3837-3860, 1993.
Dyck and Silva, "The use of ping-pong balls and latex tubing for sampling the helium content of lake sediments," *Journal of Geochemical Exploration*, 14:41-48, 1981.
Karp, "A diffusive sampler for passive monitoring of volatile organic compounds in ground water," *Ground Water*, 31(5):735-739, 1993.

(Continued)

*Primary Examiner*—Daniel S Larkin
(74) *Attorney, Agent, or Firm*—Fulbright & Jaworski L.L.P.

(57) ABSTRACT

A gas sampling system having a storage chamber configured to store a gas; a water-impermeable, gas-permeable surface; and an isolating system. The isolating system is configured to have a first and a second position, and the storage chamber is in fluid communication with the water-impermeable, gas-permeable surface when the isolating system is in a first position. The storage chamber is not in fluid communication with the water-impermeable, gas-permeable surface when the isolating system is in the second position. The gas sampling system also has a gas displacement system configured to displace the gas from the storage chamber.

23 Claims, 3 Drawing Sheets

OTHER PUBLICATIONS

McCarthy et al., "Transport of volatile organic compounds across the capillary fringe," *Water Resources Research*, 29:1675-1684, 1993.

Pearson et al., "Correction of ground-water chemistry and carbon isotopic composition for effects of $CO_2$ outgassing," *Geochimica Cosmochimica Acta*, 42:1799-1807, 1978.

Sanford et al., "Dissolved gas tracers in groundwater: Simplified injection, sampling, and analysis," *Water Resources Research*, 32(6):1635-1642, 1996.

Spalding and Watson, "Measurement of dissolved $H_2$, $0_2$, and $CO_2$ in groundwater using passive samplers for gas chromatographic analyses," *Environ. Sci. Technol.*, 40:7861-7867, 2006.

Stephenson et al., "Measurement of advective water velocity in lake sediment using natural helium gradients ," *Journal of Hydrology*, 154:63-84, 1994.

Theirrin et al, "A ground-water tracer test with deuterated compounds for monitoring in situ biodegradation and retardation of aromatic hydrocarbons," *Ground Water*, 33:469-475, 1995.

Vroblesky et al., "Locating VOC contamination in a fractured-rock aquifer at the ground-water/surface-water interface using passive vapor collectors," *Ground Water*, 34(2):223-230, 1996.

Wilson et al., "Dissolved Gas Evidence for Denitrification in the Linconshire Limestone Groundwater, Eastern England," *Journal of Hydrology*, 113:51-60, 1990.

METHOD AND SYSTEM FOR SAMPLING DISSOLVED GAS

This application claims priority to U.S. Provisional Patent Application No. 60/774,208, filed Feb. 17, 2006.

BACKGROUND OF THE INVENTION

I. Field of the Invention

The present invention relates generally to the measurement of dissolved gases. More particularly, the present invention relates to a method and system for quantitative measurement of dissolved gases, particularly dissolved gases present in groundwater.

II. Background of the Invention

Dissolved gases in groundwater can originate from equilibration with the atmosphere, incorporation of excess air during unsaturated zone migration, and production of radiogenic, chemical, or biological processes. Typical groundwater gases include $N_2$, $N_2O$, $NO$, $O_2$, $CO_2$, $CH_4$, and $H_2S$; and smaller concentrations of noble gases such as Ar, He, Kr, Rn, Ne, and Xe. While some are relatively inert in aquatic systems and can serve as hydrogeological tracers, others are actively involved in significant biogeochemical processes, playing a major role in the chemical evolution of groundwater and global geochemical cycles. Thus, the quantitative measurement of dissolved gases in groundwater can provide insight into transport and biogeochemical processes in aquifers.

The routine use of dissolved gas concentrations is becoming increasingly common in a number of fields such as geochemical exploration, seismology, paleoclimatology, age-dating of young groundwater, groundwater tracers, environmental assessment of oil and gas production, and measurement of volatile organic compound contaminants (e.g., gasoline constituents and chlorinated solvents). Monitored natural attenuation is becoming an increasingly popular remediation strategy at industrial sites with soil and/or groundwater contamination by organic contaminants (e.g. oil and gas, chlorinated solvents, etc.). Accurate and reliable data are required to demonstrate to regulators that sufficient biodegradation occurs. Regulators look for both a decrease in contaminant concentrations and evidence that these contaminants are degrading, ideally to $CO_2$ and $CH_4$ degradation end-products. Measurement of these gases is also valuable for interpretation of sub-surface chemical and biogeochemical processes and robust mass balance calculations.

Despite their value, dissolved gas analyses are often underutilized in geochemical investigations, largely because routine sampling and analytical procedures are not available. Sampling is often onerous and sample integrity compromised by degassing during sampling and manipulation for analysis.

The most commonly used sampling protocol involves pumping groundwater into a vial (with minimal atmospheric contact) and transporting the water sample to the laboratory where headspace partitioning and gas chromatographic analysis of the headspace are conducted. Degassing is often caused by decreased hydrostatic pressures during pumping, with bubbles often visible in clear pump tubing. This causes gas sample loss and a negative sample bias. Selective partitioning of more volatile gases can also result in variable sample bias. The use of peristaltic pumps in dissolved gas sampling can result in a loss of up to 10-20% of the sample due to degassing. Also, pumping often alters the natural chemical gradients and produces vertically mixed water samples from different layers of the aquifer. In addition to gas exsolution during sampling, traditional gas-sampling methods require the extraction of gases by headspace partitioning prior to gas chromatographic analysis. This procedure is time-intensive and has the potential for loss of sample due to manipulation. Ideally, groundwater gas concentrations should be sampled under insitu hydrostatic and dissolved gas pressures to ensure no degassing occurs.

Wilson (Wilson et al., *Journal of Hydrology* 1990, 113, 51-60) and Castro (Castro et al., *Water Resources Research* 1998, 34, 2467-2483) describe attempts to eliminate atmospheric degassing by isolating water samples in crimped lengths of copper tubing. Others have described a sophisticated apparatus with an evacuated vacuum flask attached to an evacuated side arm (Pearson et al., *Geochimica Cosmochimica Acta* 1978, 42, 1799-1807; and Dunkle Shapiro et al., *Water Resources Research* 1993, 29, 3837-3860). The use of gas tight syringes to sample water directly from pump tubing at the surface to eliminate atmospheric contamination has also been described (McCarthy et al., *Water Resources Research* 1993, 29, 1675-1683; and Theirrin et al, *Ground Water* 1995, 33, 469-475), however, samples still experience degassing while they are pumped from the groundwater zone to ground surface. Still further, an ampoule fusing process has been developed by United States Geological Survey researchers for collection of gas samples. Relatively sophisticated and specialized equipment is required to extract the sample from tubing or ampoules prior to analysis.

More recent methodologies eliminate atmospheric contact and attempt to eliminate degassing of the sample due to depressurization caused by pumping to ground surface. A down-hole variation on the copper tube sampling method has been used, and water samples for $CH_4$ analysis have also been collected using down-hole syringes.

Still more recently, a number of in situ sampling prototypes have been developed, including samplers incorporating water filled diffusion cells, however these methods do not eliminate the need for head-space partitioning in the laboratory with associated expense and potential for lack of accuracy.

Sorbent samplers, containing an absorbent material in a gas-filled chamber surrounded by a water-impermeable/vapour permeable membrane, have also been developed for monitoring volatile and semi-volatile compounds in water. Sorbent samplers are limited to volatile organic compound analysis and often require a solvent extraction and calibration step in the lab prior to analysis. For example, U.S. Pat. No. 5,922,974 describes an apparatus for extracting soil gases from the earth and concentrating the gases within a resin or molecular sieve. The resin must be transported to a laboratory and heated to release and analyze the collected gas.

Simple gas-filled diffusion cells have been used in measuring dissolved gas concentrations. For example, ping-pong balls covered with latex tubing have been utilized in analysis of helium in lake sediments (Dyck and Silva, *Journal of Geochemical Exploration* 1981, 14, 41-48; and Stephenson et al., *Journal of Hydrology* 1994, 154, 63-84). Although this approach provides in-situ gas sampling, the gas sample must later be transferred into a gas-tight syringe for transport to the analytical laboratory.

In summary, a variety of in situ passive-diffusion gas sampling methods have been used historically in surface water bodies and more recently in surface water-sediment interfaces. In addition to being more efficient in the field, these methods eliminate the need for a headspace partitioning step in the lab (and the associated lack of accuracy). However, passive diffusion sampler use in ground water has been limited as such samplers require either extensive machining, sample manipulation after being brought into the laboratory, or have limited depths at which they can be employed.

Samplers have been developed which include on-site analysis systems. For example, U.S. Pat. No. 6,272,938 provides a device for monitoring of Volatile Organic Compounds in groundwater, which has a gas sensor within the device, or which is connected to a gas chromatograph to provide immediate analysis of groundwater contaminants. U.S. Patent Publication 2004/0129058 provides a vapour trap for installation within the floor of a facility to monitor the accumulation of VOC's. The vapour trap is continuous with an organic vapour analyzer, and provides a sampling pump for drawing gas samples from the vapour trap. These devices are not intended to measure dissolved gas concentrations.

It is, therefore, desirable to provide an in situ dissolved gas sampler that simplifies the steps and/or improves efficiency of sample collection, sample storage, and analysis. More specifically, it is desirable to provide an efficient, cost-effective gas sampler that does not compromise sample integrity, require on-site analytical equipment, pumps, or the installation of semi-permanent or permanent equipment at the test site.

SUMMARY OF THE INVENTION

In accordance with a first aspect of the invention, there is provided a system for use in collecting a gas sample from a test or measurement environment and in storing the collected gas sample. The system comprises a storage chamber for collecting and storing a gas sample; a water-impermeable, gas permeable surface associated with the storage chamber to prevent flow of water and permit diffusion of gases into the storage chamber; an isolating system for selectively isolating the storage chamber from the gas permeable surface so as to selectively collect or store gas within the storage chamber; and a gas displacement system associated with the storage chamber for displacing gas from the storage chamber.

In one embodiment, the gas displacement system includes a plunger slidably disposed within the storage chamber and a port within the storage chamber through which gas is displaced upon depression of the plunger. In a further embodiment, the plunger is of a length at least equal to the axial length of the storage chamber, and the system may further comprise a locking system for locking the slidable position of the plunger.

In another embodiment, the system further comprises a diffusion chamber continuous with the storage chamber, wherein the gas permeable surface forms a portion of the diffusion chamber and wherein the adjustment system selectively isolates the storage chamber from the gas permeable surface by isolating the storage chamber from the diffusion chamber. The adjustment system may include a plunger slidably disposed within the storage and diffusion chambers.

In a further embodiment, the inner diameter of the diffusion chamber is greater than the inner diameter of the storage chamber, and the plunger includes a tip sized to correspond with the inner diameter of the storage chamber such that when the tip of the plunger is disposed within the storage chamber, gas within the storage chamber is effectively sealed from the diffusion chamber, and when the tip of the plunger is disposed within the diffusion chamber, gas is able to flow across the gas-permeable surface, past the plunger tip, and into the storage chamber.

Still further, the diffusion chamber may be a gas-permeable, inert cylinder surrounded by a gas-permeable water-impermeable membrane. The gas-permeable, inert cylinder may be a cylinder of sintered metal that minimizes internal volume while providing good support for the membrane.

The gas-permeable, water-impermeable membrane may be silicone tubing, and the storage chamber may be defined by an inert, water-impermeable, gas-impermeable cylinder, which may be a glass cylinder.

In a second aspect of the invention, there is provided a method for collecting a gas sample from a sampling environment, comprising the steps of:
(a) placing a storage chamber having a water-impermeable, gas-permeable diffusion surface in a sampling environment for a period of time to allow gases present in the sampling environment to passively diffuse through the diffusion surface into the storage chamber;
(b) removing the storage chamber from the sampling environment; and
(c) sealing the gas within the storage chamber from further contact with the diffusion surface.

In certain embodiments, the gas is sealed in the storage chamber immediately after the storage chamber has been removed from the sampling environment. In one embodiment of the invention, the method may further comprise the step of displacing the gas from the storage chamber directly into a gas chromatograph for analysis. The displacement of gas may be achieved by a plunger slidably engaged within the storage chamber. The slidable position of the plunger may lockable.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein.

DETAILED DESCRIPTION OF THE INVENTION

Embodiments of the present invention provide a system and method for collection and storage of a gas sample from a test or sampling environment, and a method and system for: obtaining a gas sample from a sampling environment; storing the sample during transportation to an analysis site; and injection of the gas sample into an analytical instrument. In certain embodiments, the gas sample is directly injected into an analytical instrument. In particular, the ability to passively collect a gas sample at a test site, and to store the sample for a period of time without altering the partial pressures of the collected gases, facilitates an accurate and absolute determination of dissolved gas concentration. Embodiments of the present invention are particularly useful in obtaining gas samples from soil or groundwater.

I. OVERVIEW

A gas sampler in accordance with certain embodiments of the present invention comprises a storage chamber, and a water impermeable, gas permeable surface associated with the storage chamber, thereby permitting gas diffusion from a test or measurement environment into the storage chamber. In certain embodiments, an isolating system is present within the gas sampler for selectively isolating the gas permeable surface from the storage chamber. The gas sampler also comprises a displacement system for ejecting gas from the storage chamber in certain embodiments.

In use, a system in accordance with embodiments of the invention may be placed within a test or sampling environment such as a monitoring well or other groundwater source, allowing gases to passively diffuse from the groundwater into the storage chamber of the sampler until the gases within the storage chamber reach equilibrium with those in the groundwater. According to certain embodiments, once equilibrium has been reached, the isolating system is adjusted to isolate the gas permeable surface from the storage chamber, thereby sealing the equilibrated gas within the storage chamber. The sampler may then be transported to the laboratory, where the displacement system may be applied to eject gas from the storage chamber directly into a gas chromatograph for analysis. In certain embodiments, the sampler may be used with a downhole total dissolved gas pressure meter to permit calculation of absolute gas concentrations in the groundwater source.

II. STRUCTURE OF DISCLOSED EMBODIMENT

Figure 1:
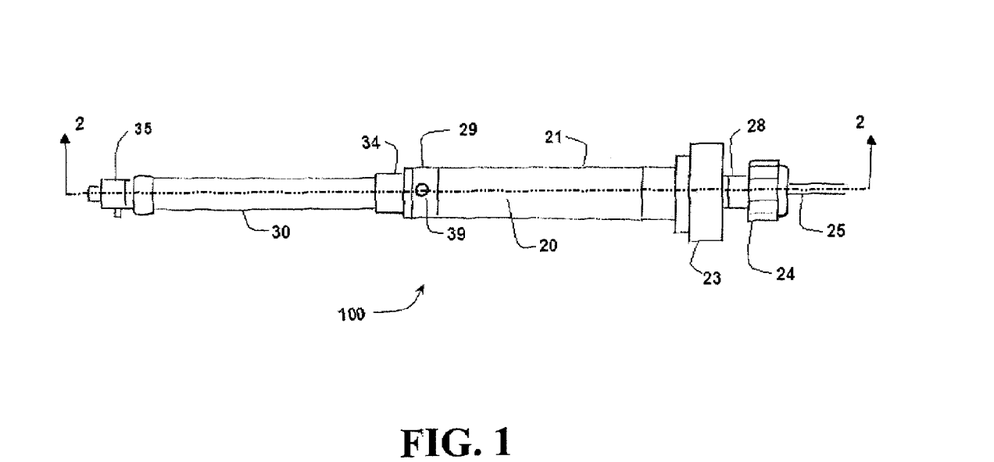
FIG. 1 is a side view of a dissolved gas sampler in accordance with an embodiment of the invention; and, FIG. 2 is a cross-section view of the embodiment of FIG. 1 in a first position.
Figure 2:
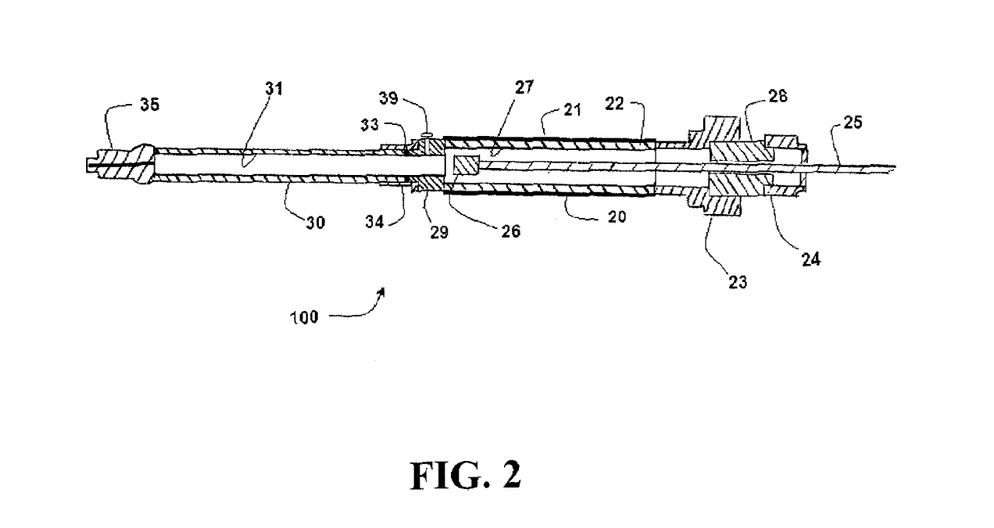
Figure 3:
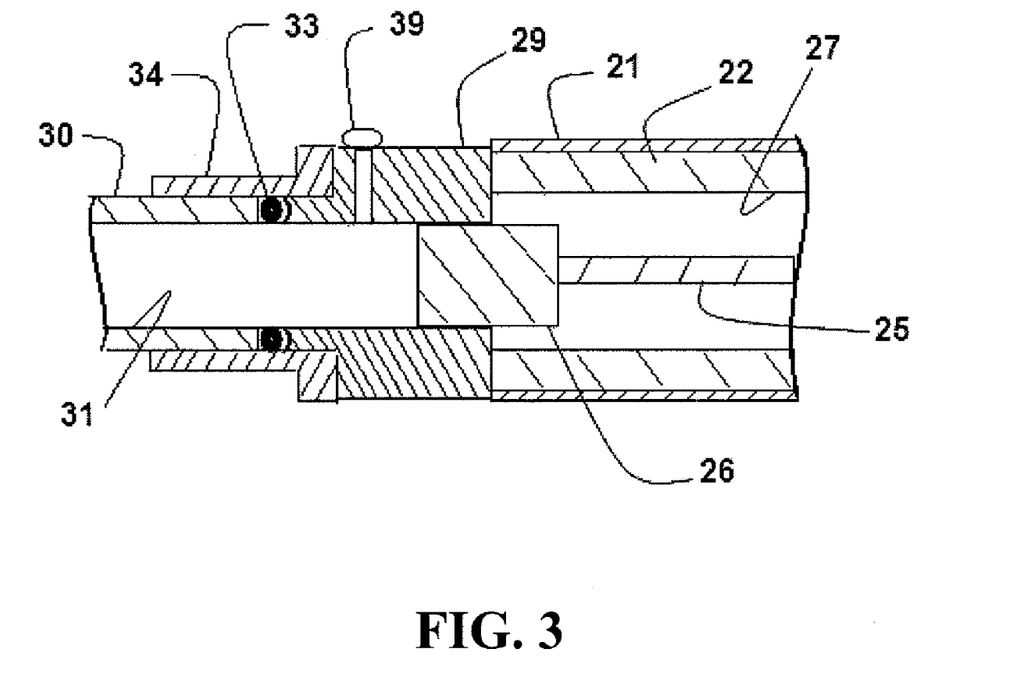
FIG. 3 is a detail cross-section view of the embodiment of FIG. 1 in a second position; and, FIG. 4 is a schematic diagram of a method for obtaining a groundwater sample in accordance with an embodiment of the invention.

Referring initially to FIGS. 1-3, one embodiment of a sample system 100 in accordance with the present invention is shown. In this embodiment, a diffusion chamber 20 is coupled to a storage chamber 30. Diffusion chamber 20 comprises a membrane 21 disposed around a support member 22 in this embodiment. In the embodiment shown, membrane 21 is water-impermeable and gas-permeable and support member 22 is gas-permeable. A plunger rod 25 and plunger tip 26 are slidably disposed within storage chamber 30 and diffusion chamber 20 to serve as an isolating system and a gas displacement system. In the embodiment shown, storage chamber 30 is impermeable to both water and gas. In this embodiment, plunger tip 26 may be moved from an open position (shown in FIG. 2) to a closed position (shown in FIG. 3). If plunger tip 26 is in the open position, storage chamber 30 is in fluid communication with membrane 21, and diffusion chamber 20 permits passive diffusion of gas across membrane 21 and support member 22 into the diffusion chamber 20 and storage chamber 30. If plunger tip 26 is in a closed position, storage chamber 30 is not in fluid communication with membrane 21, and gas that enters diffusion chamber 20 will be restricted from entering storage chamber 30.

In the embodiment shown, support member 22 comprises a cylinder of sintered metal, which provides an inert support member having minimal volume and maximal surface area for diffusion of gases. In this embodiment, the inner diameter 27 of support member 22 is continuous with storage chamber 30, which comprises a glass cylinder that is open at one end so as to be continuous with the diffusion chamber. In the embodiment shown, storage chamber 30 includes a port 35, which may be an adjustable valve having a closed position so as to prevent gas escape during collection, storage, and transportation, and an open position to permit ejection of the sample from the storage chamber by the displacement system.

As shown in FIGS. 2 and 3, inner diameter 27 of diffusion chamber 20 is greater than inner diameter 31 of storage chamber 30 to permit passage of gas past plunger tip 26 and into storage chamber 30 during gas sampling, as will be explained below.

In this embodiment, plunger tip 26 is disposed on plunger rod 25 that is slidably positioned within diffusion chamber 20 and storage chamber 30 so as to permit slidable movement therewithin between a sampling position and a storage position. In the embodiment shown, inner diameter 27 of diffusion chamber 20 is greater than inner diameter 31 of storage chamber 30 and plunger tip 26 is freely slidable within diffusion chamber 20 in the sampling or open position. However, in this embodiment, plunger tip 26 forms a seal with inner diameter 31 of storage chamber 30 when slidably positioned therewithin in a closed or storage position, as shown in FIG. 3. When plunger tip 26 is in the storage position, gas is restricted from escaping from storage chamber 30.

With reference to FIG. 2, in the sampling position, plunger tip 26 is located just inside diffusion chamber 20, providing a continuous volume through both diffusion chamber 20 and sampling chamber 30. With reference to FIG. 3, in the storage position, plunger tip 26 is located just within storage chamber 30, thereby isolating gas present in storage chamber 30 from diffusion chamber 20.

In the embodiment shown, diffusion chamber 20 and storage chamber 30 are coupled by coupling members 29 and 34. In this embodiment, coupling member 29 is a female straight pipe thread connector and coupling member 34 is a male straight pipe thread connector. This embodiment also comprises a sealing member 33 disposed between coupling members 29 and 34. In the embodiment shown, sealing member 33 is a viton o-ring.

On the end of diffusion chamber 20 opposite of storage chamber 30, this embodiment of sampling system 100 comprises a coupling member 23 which may be used to couple sampling system 100 to a protective cage (not shown) during use. The embodiment shown also comprises an adapter 28 that is coupled to a locking mechanism 24 that may be used to lock plunger rod 25 in place. In FIGS. 1 and 2, the full length of plunger rod 25 is not shown for purposes of clarity in other features. The portion of plunger rod 25 extending past locking mechanism 24 is preferably at least equal in length to the combined axial length of the storage and diffusion chambers such that the volume of the stored gas within the storage chamber 30 can be completely displaced from the storage chamber through port 35 by full depression of the plunger 25.

The embodiment shown in FIGS. 1-3 also comprises a pressure relief valve 39. Pressure relief valve 39 can be set to relieve excessive gas pressure that may damage or rupture components (such as storage chamber 30 or diffusion chamber 20) of sample system 100. For example, sample system 100 may be placed at significant depths during sampling, and in certain embodiments has been used at depths up to 100 meters below the surface of the earth. At significant depths, the pressure differential between dissolved gases partitioned into sample system 100 and the external environment may become significant as sample system 100 is brought to the surface. Pressure relief valve 39 may therefore be set to relieve the internal pressure of sample system 100 at a pressure differential that is within the design limits of the components and thereby prevent damage to sample system 100. Although one pressure relief valve 39 is shown extending through coupling member 29 in the embodiment of FIGS. 1-3, other embodiments may have multiple pressure relief valves in other locations, such as coupling member 23.

The incorporation of support member 22, along with other features such as pressure relief valve 39, allow sample system 100 to be used at greater depths and higher differential dissolved gas and hydrostatic pressures than would otherwise be possible. For example, support member 22 can restrict membrane 21 from collapsing or significantly deforming as the external pressure increases while sample system 100 is being lowered into a monitoring well or other groundwater source. In the embodiment shown, support member 22 provides a rigid structural support for membrane 21, which may be comprised of a flexible material. The use of support member 22, along with pressure relief valve 39, can therefore increase the hydrostatic and dissolved gas pressures (and therefore the depth) at which sample system 100 can be operated.

III. METHOD FOR COLLECTION AND STORAGE OF DISSOLVED GAS

Figure 4:
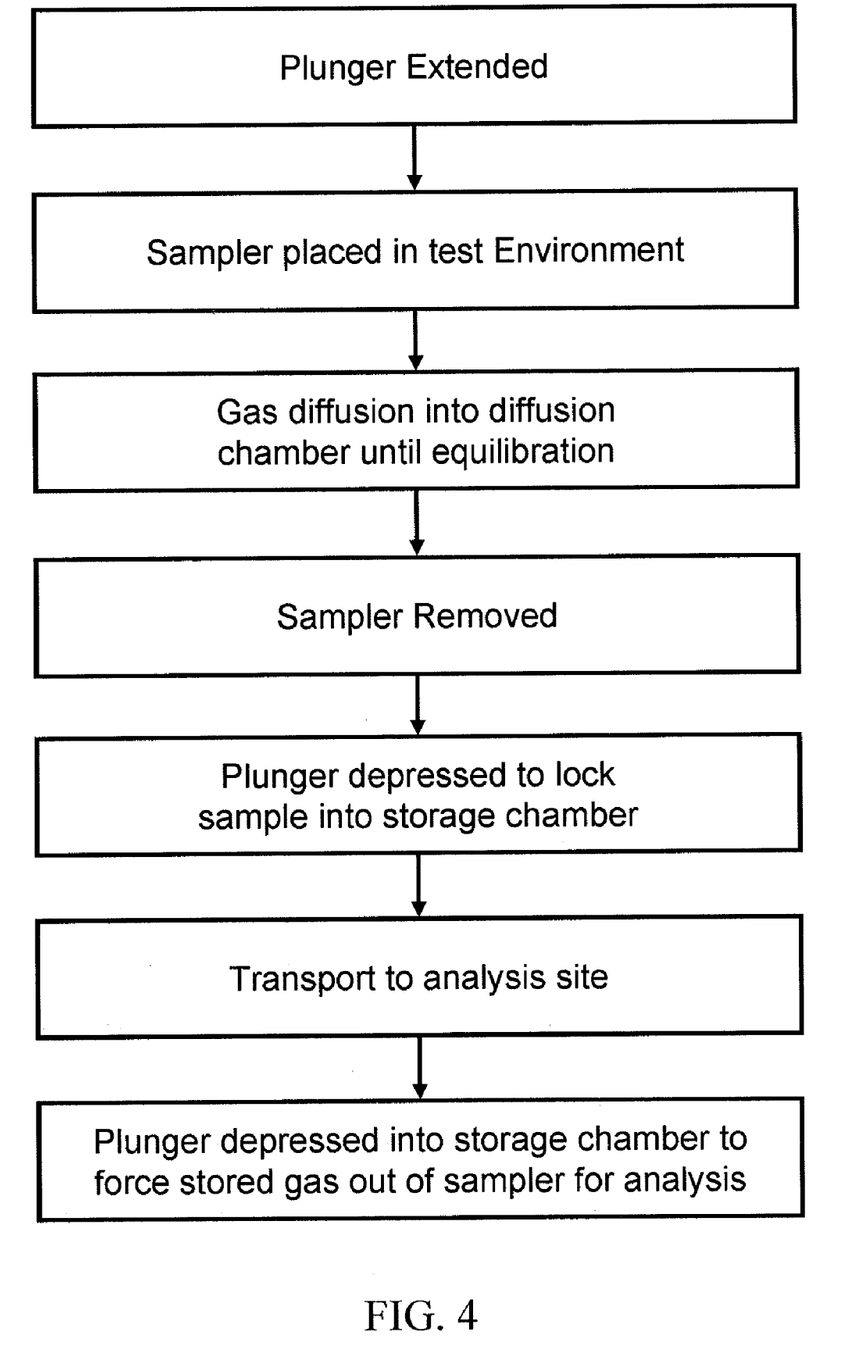

With reference to FIG. 4, a method for collecting and storing a sample of dissolved groundwater gas in accordance with an embodiment of the invention is described.

Initially, the system with the plunger in the sampling position is exposed to a source of groundwater, for example by lowering it downhole. Due to the difference in partial pressures of various gases present in the groundwater and in the diffusion chamber 20, groundwater gases will begin to diffuse through the gas-permeable membrane 21 and support member 22 to enter the diffusion and storage chambers. Similarly, gases within the chambers will diffuse into the groundwater. In essence, all gases present will diffuse according to their concentration gradients and partition into the sampler until the gases inside the sampler is in equilibrium with the gases dissolved in the groundwater. The time needed for gas concentration equilibrium is dependent on subsurface conditions and can be estimated using theoretical calculations if site conditions are available, and can be verified experimentally. The equilibrium time may vary greatly depending on conditions, and could be hours, days, weeks, or months. With extended equilibrium times, sample system 100 can provide a temporally-averaged gas concentration reading, rather than just a snapshot.

At some point after diffusion has been initiated, and preferably after equilibrium has been reached in certain embodiments, sample system 100 is removed from the sampling environment and plunger rod 25 and plunger tip 26 are depressed slightly into the storage position. In this position, plunger tip 26 forms a gas-tight seal with the inner surface of storage chamber 30, thereby isolating diffused gas within storage chamber 30 with only a very slight excess of gas pressure. In certain embodiments, this is preferably done immediately after ending the exposure to groundwater.

Locking mechanism 24 may be present to maintain plunger tip 26 in a desired position, and when locked in the storage position, the sample may be stored for a period of time to enable transportation of the system and the sample to the laboratory. Once sampling system 100 has been transported to the laboratory or other analysis location, locking mechanism 24 may be unlocked and port 35 opened so that plunger rod 25 can be depressed and plunger tip 26 can eject gas from storage chamber 30. In certain embodiments, a needle (not shown) may be coupled to port 35 and the gas may be injected into a gas chromatograph.

IV. ADDITIONAL EMBODIMENTS

Although the embodiments depicted in FIGS. 1-4 have been disclosed for exemplary purposes, it is recognized that many other embodiments are possible and remain within the spirit and scope of the invention. For example, a sampling system may be designed without a diffusion chamber, but wherein the water-impermeable, gas-permeable surface may be brought into and out of contact with the storage chamber by other means. In addition, the gas displacement system may be replaced, for example, with an alternate evacuation system that does not incorporate a plunger.

Further modifications may be made to the design such that samples may be obtained under various conditions. For example, when sampling under high hydrostatic pressures, the storage chamber may be machined from stainless steel, and a controlled pressure relief valve may be present to allow for excess gas pressure release as the external hydrostatic pressure decreases when the sample system if removed from the sampling environment.

V. METHOD FOR ANALYSIS OF STORED GAS SAMPLE

Numerous methods of analyzing gas samples are available. One popular method of analysis is by gas chromatography. Embodiments of the present invention simplify analysis by gas chromatography because the sample can be injected directly from the system into the gas chromatograph. As a result, no sample preparation or manipulation (e.g., headspace partitioning) is required prior to analysis. As shown in FIG. 1, the present invention may include a port 35 to permit direct injection of the gas sample from storage chamber 30, into a gas chromatograph (GC). Following analysis of the sample, the system may be redeployed in the field for collection of a further gas sample.

Generally, GC analysis of a gas sample ejected from the storage chamber will provide the relative composition of gases in the sample, but will not provide absolute concentrations. The estimation of absolute concentrations of the gases may be accomplished using an estimate of the total gas pressure in the groundwater. In one embodiment of the invention, a total dissolved gas pressure probe (TDGP) is placed into the well immediately before or after removing the gas sampler. The TDGP probe generally takes about 15 minutes or less to reach equilibrium and the total dissolved gas pressure may be recorded.

Multiplication of relative gas composition and total dissolved gas pressure will provide absolute gas concentrations. This approach considers "gas-charging" in the subsurface and avoids the bias associated with the current practice of estimating absolute concentrations by headspace partitioning (which results in groundwater gas concentrations being underestimated if their concentrations are high with respect to water equilibrated with the atmosphere (WEA), or overestimated if they are higher in WEA than in the groundwater).

VI. SPECIFIC DESIGN OF ONE EMBODIMENT OF THE GAS SAMPLER

One aspect of the invention will now be described by the following example, which is provided to disclose one specific embodiment of the invention. The following example is not intended to limit other possible embodiments of the invention, which will be readily apparent to those of skill in the art.

Example 1

A 1 mL Hamilton™ sample lock gas tight syringe was modified to become a storage chamber, which contains the sample when the rod is depressed such that the plunger rests within the storage chamber just before the connection point between the diffusion chamber and the storage chamber (i.e., the 'storage' position). Machined threads maintain the position of the rod and plunger, thereby preventing movement of the plunger and potential gas loss during diffusion of the stored gas. In the present example, the lock valve used can withstand up to 200 pounds per square inch of pressure. A 5/16" 32 UNEF female straight pipe thread connection was used to connect the syringe to the diffusion chamber.

To form the diffusion chamber, a length of silicone tubing (Tygon™ sanitary silicone tubing 0.625" O.D.×½" I.D.) was affixed around a sintered metal tube (GKN Sinter Metal ½" O.D.×¼" I.D.) to provide a gas-tight seal as described below. It is recognized that other materials (for example, polyethylene or teflon) may be substituted for silicone with comparable results.

A 3" piece of stainless steel sintered metal tubing (50% porosity) was welded to two machined pieces of solid stainless steel tubing (½" O.D.). The end attaching to the storage chamber 30 was machined from a 5/16" 32 UNEF thread male straight pipe thread connector with a machined groove flush to the end of the syringe that houses a viton rubber o-ring. At the opposite end of the barrel, the solid stainless steel tubing included: a threaded portion to permit the sampler to be anchored within a protective cage during installation and retrieval; and a threaded portion for the attachment of a straight through reducer fitting (½" to ⅛") (Swage-Lock) with Teflon™ ferrules (⅛") to hold the plunger in place. The silicone tubing was stretched over the stainless steel skeleton and secured at both ends with silicone sealant and nylon thread.

The plunger was constructed from stainless steel, with a machined Teflon™ plunger tip connected to the plunger to form a gas-tight seal when located inside glass syringe in its 'storage' position.

The above-described embodiments of the present invention are intended to be examples only. Alterations, modifications and variations may be effected to the particular embodiments by those of skill in the art without departing from the scope of the invention, which is defined solely by the claims appended hereto.

All of the systems and/or methods disclosed and claimed herein can be made and executed without undue experimentation in light of the present disclosure. While the systems and methods of this invention have been described in terms of preferred embodiments, it will be apparent to those of skill in the art that variations may be applied to the systems and/or methods and in the steps or in the sequence of steps of the method described herein without departing from the concept, spirit and scope of the invention. More specifically, it will be apparent that certain related components or steps may be substituted for the components described herein while the same or similar results would be achieved. All such similar substitutes and modifications apparent to those skilled in the art are deemed to be within the spirit, scope and concept of the invention as defined by the appended claims.

VII. REFERENCES

The following references, to the extent that they provide exemplary procedural or other details supplementary to those set forth herein, are specifically incorporated herein by reference:

Wilson et al., *Journal of Hydrology* 1990.
Castro et al., *Water Resources Research* 1998.
Pearson et al., *Geochimica Cosmochimica Acta* 1978.
Dunkle Shapiro et al., *Water Resources Research* 1993.
McCarthy et al., *Water Resources Research* 1993.
Theirrin et al, *Ground Water* 1995.
U.S. Pat. No. 5,922,974.
Dyck and Silva, *Journal of Geochemical Exploration* 1981.
Stephenson et al., *Journal of Hydrology* 1994.
U.S. Pat. No. 6,272,938.
U.S. Patent Publication 2004/0129058.

The invention claimed is:

1. A system for collecting dissolved gas, the system comprising:
   a storage chamber for collecting and storing a gas sample;
   a water-impermeable, gas-permeable surface associated with the storage chamber to prevent diffusion of water and permit diffusion of gas into the storage chamber;
   an isolating system for selectively isolating the storage chamber from the water-impermeable, gas-permeable surface so as to selectively collect or store gas within the storage chamber;
   a gas displacement system associated with the storage chamber for displacing gas from the storage chamber, wherein the gas displacement system includes a plunger slidably disposed within the storage chamber and a port within the storage chamber through which gas is displaced upon depression of the plunger; and
   a locking system for locking the slidable position of the plunger.

2. The system as in claim 1 wherein the plunger is of a length at least equal to the axial length of the storage chamber.

3. A system for collecting dissolved gas, the system comprising:
   a storage chamber for collecting and storing a gas sample;
   a water-impermeable, gas-permeable surface associated with the storage chamber to prevent diffusion of water and permit diffusion of gas into the storage chamber;
   an isolating system for selectively isolating the storage chamber from the water-impermeable, gas-permeable surface so as to selectively collect or store gas within the storage chamber;
   a gas displacement system associated with the storage chamber for displacing gas from the storage chamber; and
   a diffusion chamber continuous with the storage chamber, wherein the water-impermeable, gas-permeable surface forms a portion of the diffusion chamber and wherein the isolating system selectively isolates the storage chamber from the water-impermeable, gas-permeable surface by isolating the storage chamber from the diffusion chamber and wherein the isolating system includes a plunger slidably disposed within the storage chamber and the diffusion chamber.

4. The system as in claim 3 wherein the inner diameter of the diffusion chamber is greater than the inner diameter of the storage chamber, and wherein the plunger includes a tip sized to correspond with the inner diameter of the storage chamber such that when the tip of the plunger is disposed within the storage chamber, gas within the storage chamber is effectively sealed from the diffusion chamber, and when the tip of the plunger is disposed within the diffusion chamber, gas is able to flow across the water-impermeable, gas-permeable surface, past the plunger tip, and into the storage chamber.

5. The system as in claim 3 wherein the diffusion chamber comprises a support member for the water-impermeable, gas-permeable surface.

6. The system as in claim 5 wherein the support member is a cylinder of sintered metal.

7. The system as in claim 5 wherein the gas-permeable, water-impermeable membrane is silicone tubing.

8. The system as in claim 3 wherein the storage chamber comprises an inert, water-impermeable, gas-impermeable cylinder.

9. The system as in claim 8 wherein the inert, water-impermeable, gas-impermeable cylinder is a glass cylinder.

10. The system as in claim 3 further comprising a pressure relief valve in fluid communication with the storage chamber.

11. The system as in claim 3 wherein the system is configured to collect dissolved gas from a fluid source at a depth of 100 meters or more below the surface of the earth.

12. A method for collecting a gas sample, the method comprising:
placing a storage chamber having a water-impermeable, gas-permeable diffusion surface in a sampling environment for a period of time to allow gases present in the sampling environment to passively diffuse through the diffusion surface into the storage chamber;
removing the diffusion chamber from the sampling environment; and
sealing the gas within the storage chamber from further contact with the diffusion surface.

13. The method as in claim 12, further comprising the step of displacing the gas from the storage chamber directly into a gas chromatograph for analysis.

14. The method as in claim 12 wherein gas is displaced from the storage chamber by a plunger slidably engaged within the storage chamber.

15. A gas sampling system comprising:
a storage chamber configured to store a gas:
a water-impermeable, gas-permeable surface:
an isolating system configured to have a first position and a second position, wherein the storage chamber is in fluid communication with the water-impermeable, gas-permeable surface when the isolating system is in a first position and wherein the storage chamber is not in fluid communication with the water-impermeable, gas-permeable surface when the isolating system is in the second position;
a gas displacement system configured to displace the gas from the storage chamber, wherein the water-impermeable, gas-permeable surface is disposed around a support member.

16. The gas sampling system of claim 15 wherein the water-impermeable, gas-permeable surface is silicone tubing.

17. The gas sampling system of claim 15, wherein the support member restricts the water-impermeable, gas-permeable surface from collapsing when the gas sampling system is placed at a depth of 100 meters or more below the surface of the earth.

18. The gas sampling system of claim 15 further comprising a pressure relief valve in fluid communication with the storage chamber and the water-impermeable, gas-permeable surface when the isolating system is in the first position.

19. The gas sampling system of claim 15 wherein the support member is a gas-permeable, inert cylinder.

20. The gas sampling system of claim 19 wherein the gas-permeable, inert cylinder comprises sintered metal.

21. The gas sampling system of claim 15 wherein the isolating system comprises a plunger slidably disposed to engage the storage chamber.

22. The gas sampling system of claim 21 wherein the isolating system further comprises a locking mechanism configured to lock the plunger in a stationary position.

23. The gas sampling system of claim 15 wherein the gas displacement system comprises a plunger configured to slidably engage the storage chamber.

* * * * *